US010065876B2

(12) United States Patent
Barnard

(10) Patent No.: US 10,065,876 B2
(45) Date of Patent: Sep. 4, 2018

(54) ALGAL SYSTEM FOR IMPROVING WATER QUALITY

(71) Applicant: Malcolm A Barnard, Johns Creek, GA (US)

(72) Inventor: Malcolm A Barnard, Johns Creek, GA (US)

( * ) Notice: Subject to any disclaimer, the term of this patent is extended or adjusted under 35 U.S.C. 154(b) by 0 days.

(21) Appl. No.: 14/898,111

(22) PCT Filed: Jun. 12, 2014

(86) PCT No.: PCT/US2014/042193
§ 371 (c)(1),
(2) Date: Dec. 11, 2015

(87) PCT Pub. No.: WO2014/201298
PCT Pub. Date: Dec. 18, 2014

(65) Prior Publication Data
US 2016/0122217 A1    May 5, 2016

Related U.S. Application Data

(60) Provisional application No. 61/834,088, filed on Jun. 12, 2013.

(51) Int. Cl.
*C02F 3/32* (2006.01)
*A01N 65/03* (2009.01)
(Continued)

(52) U.S. Cl.
CPC ............. *C02F 3/322* (2013.01); *A01N 65/03* (2013.01); *C02F 2101/105* (2013.01);
(Continued)

(58) Field of Classification Search
CPC ............... C02F 3/322; C02F 2101/105; C02F 2101/163; C02F 2203/006;
(Continued)

(56) References Cited

U.S. PATENT DOCUMENTS 3,598,726 A * 8/1971 Welch ............ C02F 3/082
210/151
4,966,096 A * 10/1990 Adey ............ A01K 63/04
119/226
(Continued)

FOREIGN PATENT DOCUMENTS

CN      202680233 U  *  1/2013
KR      2005/024728 A  *  3/2005

OTHER PUBLICATIONS

Appendix A, Entry to the Stockholm Junior Water Prize, "Utilization of Spirogyra grevilleana as a Method of Algal Filtration for Reduction of Limnotic *Escherichia coli* Levels," Malcolm Barnard, Georgia (2014).*

(Continued)

*Primary Examiner* — Fred Prince
(74) *Attorney, Agent, or Firm* — Coursey IP Law LLC; R. Stevan Coursey

(57) ABSTRACT

The disclosure describes an algal system for improving water quality through the use of algae. In example embodiments, the algal system comprises an elongate device including algae enclosed therein and capable of reducing at least the levels of nitrates and phosphates in water directed through the device. The algae may be capable of also reducing *E. coli* bacteria, other bacteria, and viruses in the water. Preferably, the algae comprises a filamentous green algae, including without limitation, *Spirogyra grevilleana* algae. In one example embodiment, the algal system comprises an elongate device and an elongate cartridge that is pre-configured to treat certain chemical compounds, bacteria, and viruses, and certain other characteristics of water. The cartridge is delivered to the site where the water is to be treated and installed in the field, possibly replacing an
(Continued)

existing cartridge. After use, algae may be processed into biofuel.

37 Claims, 5 Drawing Sheets

(51) Int. Cl.
   *C02F 101/10* (2006.01)
   *C02F 101/16* (2006.01)
(52) U.S. Cl.
   CPC .... *C02F 2101/16* (2013.01); *C02F 2101/163* (2013.01); *C02F 2203/00* (2013.01); *C02F 2203/006* (2013.01); *C02F 2203/008* (2013.01); *C02F 2303/04* (2013.01); *Y02W 10/37* (2015.05)
(58) Field of Classification Search
   CPC ............ C02F 2203/008; C02F 2101/16; C02F 2203/00; C02F 2303/04; A01N 65/03; Y02W 10/37
   USPC .................................................. 210/602, 764
   See application file for complete search history.

(56) References Cited

U.S. PATENT DOCUMENTS

| | | | | |
|---|---|---|---|---|
| 5,011,604 | A * | 4/1991 | Wilde | C02F 3/32 210/170.09 |
| 5,389,248 | A * | 2/1995 | Pare | B01D 53/84 210/151 |
| 5,851,398 | A * | 12/1998 | Adey | C02F 3/32 210/602 |
| 6,346,252 | B1 * | 2/2002 | Moigne | A01N 65/00 424/195.17 |
| 2007/0224216 | A1 * | 9/2007 | Teas | A61K 35/748 424/195.17 |
| 2011/0266215 | A1 * | 11/2011 | Robinson | C02F 1/30 210/602 |

OTHER PUBLICATIONS

Appendix B, Entry to the Stockholm Junior Water Prize, "Using an Algal Filter to Improve Water Quality," Malcolm Barnard, Georgia (2013).*

* cited by examiner

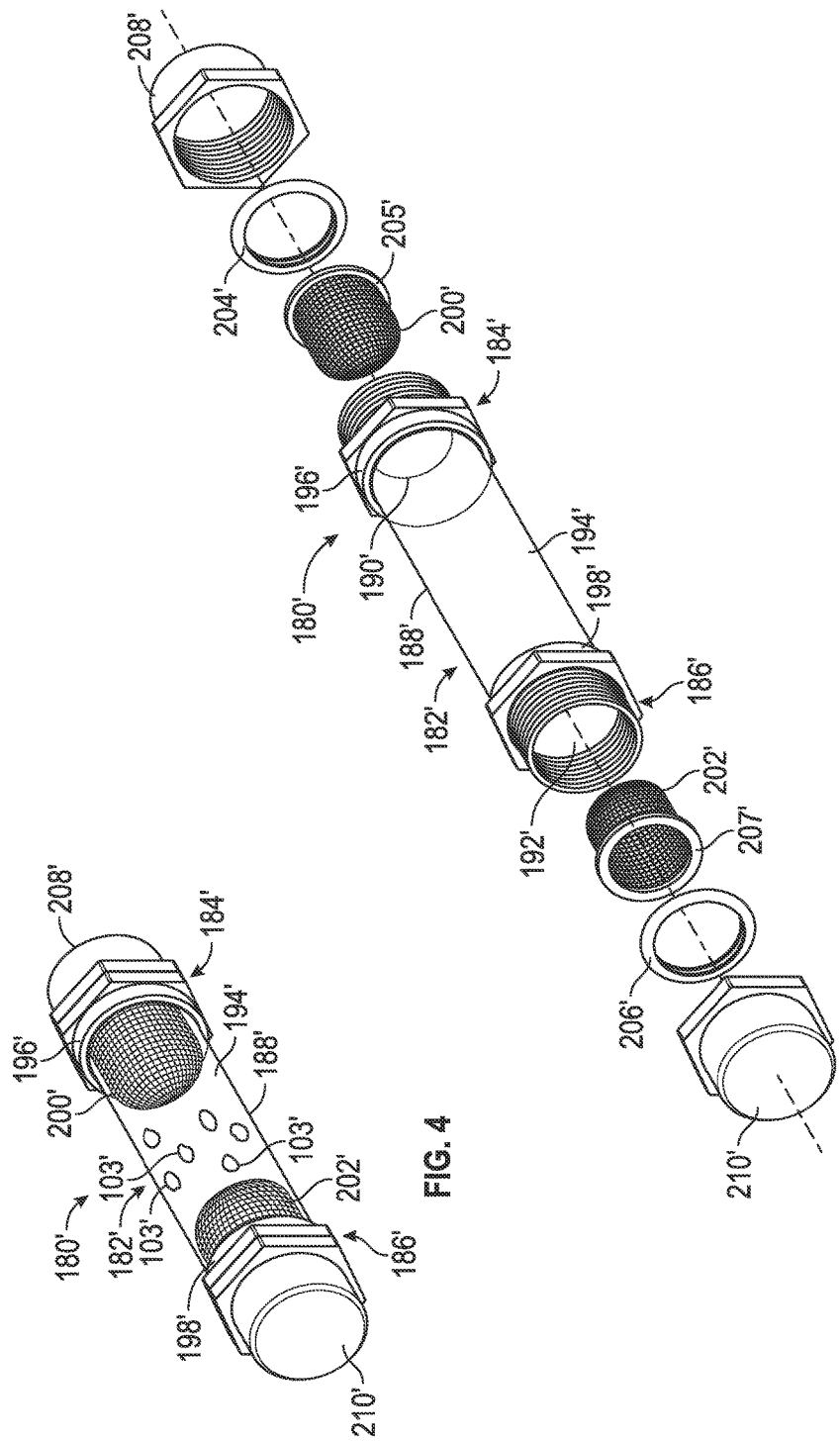

ALGAL SYSTEM FOR IMPROVING WATER QUALITY

CROSS REFERENCE TO RELATED APPLICATION

This application claims the benefit of U.S. Provisional Application No. 61/834,088, filed Jun. 12, 2013, which is incorporated herein in its entirety by this reference.

FIELD OF THE INVENTION

The present invention relates, generally, to the field of systems, including apparatuses and methods, for improving water quality.

BACKGROUND OF THE INVENTION

Freshwater ecosystems have been critical to sustaining life and establishing civilizations throughout history, as evidenced by many human settlements worldwide being concentrated near freshwater ecosystems and with over half of the world's population living within 20 kilometers of a permanent river. Unfortunately, as global population has grown, increased agricultural and industrial production combined with poor sanitation practices has led to a widespread increase in water pollution with most freshwater lakes becoming contaminated to some extent by chemical and biological contaminants or pollutants such as *Escherichia coli* (*E. coli*) and dissolved nutrients in the form of nitrogen and phosphates. Such contamination has decreased the potability of the water and the ability of fish and other wildlife to survive in these freshwater lakes.

More specifically, the pollution and contamination of freshwater lakes and corresponding reduction in water quality has occurred due, at least in part, from soil erosion, nutrient mismanagement, and pesticide mismanagement. Soil erosion reduces water quality as contaminants and debris present in the soil are carried with surface water that runs off into creeks, streams, rivers and lakes. The contaminated soil then releases its nutrient load, leaching pollutants into the water and promoting growth of autotrophic and heterotrophic microorganisms, including various algae and bacteria such as *E. coli*. Nutrients also enter creeks, streams, rivers and lakes through runoff, such as storm water from rain or melting snow, which flows from roads, rooftops, farms, and lawns picking up contaminants such as wastewater, fertilizers, lawn treatment chemicals, pesticides, and household chemicals along the way. Such polluted runoff contaminates and degrades the quality of water in creeks, streams, rivers, and lakes, and the polluted runoff can kill or damage plants, fish, and wildlife.

Excess nutrients, such as nitrogen and phosphorous, in raised concentrations increase algae productivity, especially filamentous green algae, and may contribute to out-of-control algae blooms in freshwater lakes. And, excess nitrogen and phosphorous can cause eutrophication, which is the process of increasing organic enrichment or biological productivity leading to increased algae and aquatic weed growth, oxygen shortages, and formation of carcinogens during water chlorination. The eutrophication of natural waters, caused by an increase in dissolved nutrients, is one of the most significant causes of declining water quality. Although eutrophication is a natural process of aging of lakes and water bodies, human activities can greatly accelerate eutrophication by accelerating the rate at which nutrients and organic substances enter aquatic ecosystems from their surroundings. This has occurred at Lake Victoria, the second largest lake in the world and an important water source shared by Kenya, Uganda, and Tanzania, where a surface algal mass is frequent due to increased pollution from humans and industrial waste containing phosphates and nitrates.

Similarly, in Lake Erie of the Great Lakes, phosphorus was shown to be a major nutrient contributing to and controlling phytoplankton growth. In Lake Erie, hypoxia has been directly linked to elevated in-lake total phosphorus concentrations and excessive external total phosphorus loadings. For many years, detergents having phosphates flowed into Lake Erie. Following a ban being placed on phosphates in detergents, total yearly concentrations of phosphorus and dissolved oxygen depletion rates declined significantly. As a result, algal biomass reductions were observed, especially in nuisance and eutrophic species of algae. Prior to the ban, diatom populations tended to dominate the algae species favored by nutrient rich conditions, cyanobacteria were in abundance, as well as the green algae *Cladophora* and the red algae, *Bangia*.

Excess nutrients have also been responsible for the Chesapeake Bay having massive numbers of algal blooms each spring due to fertilizer runoff from local farms and lawns. Then, as the algal blooms die off, resulting decomposition depletes life-supporting oxygen in the water and causes dead zones in the bay. According to some, such harmful algal blooms are excessive accumulations of microscopic photosynthesizing organisms (phytoplankton) that produce biotoxins or that otherwise adversely affect humans, animals, and ecosystems. Most harmful algal blooms are cyanobacteria blooms, but others are nonbacterial blooms from algae like *Cladophora*, which is known to harbor *E. coli* populations. The presence of algal masses is, therefore, often associated with elevated *E. coli* levels.

*E. coli* are heterotrophic bacteria classified as coliform. In addition to algal blooms and other organic matter, catalysts for *E. coli* growth include swelling rainfall and other atypical events. The presence of *E. coli* is also a widely used indicator of contamination originating from domestic sewage. Although for the most part *E. coli* is not pathogenic, its presence in surface water, especially at elevated levels, can indicate fecal contamination and the likelihood that pathogens such as *Salmonella*, Streptococci, *Cryptosporidium, Giardia*, and Enterovirus could be present.

Scientists and engineers have attempted to remove dissolved nutrients and improve the water quality of the Chesapeake Bay and other large bodies of water through the controlled use of algae in devices commonly referred to as Algal Turf Scrubbers ("ATS"). An algal turf is a community of organisms dominated by aggregations of unicellular to branched filamentous algae and cyanobacteria (blue-green algae). Unlike the uncontrolled overgrowth of algae in bodies of water described above, algal growth in Algal Turf Scrubber systems is controlled and beneficial rather than harmful to the water quality. Algal Turf Scrubber systems work with fresh water, brackish water, and salt water, and work in a variety of waste and industrial settings such as water quality treatment plants, farm canals, rivers, and the inside of industrial smoke stacks.

Algal Turf Scrubber systems typically include a series of filtration troughs with thin screens that catch filamentous algae. Solar powered pumps add water to the open troughs from a river or other flowing body of water. The water flows through the open troughs, being filtered along the way, and then trickles back into the flowing body of water or into a stagnant body of water, such as a bay. To keep the Algal Turf Scrubber systems running smoothly and to keep fresh algae in the systems, algae are harvested every five (5) to fifteen (15) days. The harvested algae can then be converted into biofuels such as biodiesel, gasohol, methane, and butanol.

Unfortunately, Algal Turf Scrubber systems are expensive to construct and operate. Algal Turf Systems also comprise permanent installations that require massive areas on land and on water. The average dimensions of a current land-based Algal Turf Scrubber system are 50 meters by 1,800 meters, the length of an average airport runway. To clean the Chesapeake Bay, it has been estimated that a combined 10,000 acres of land-based and floating Algal Turf Scrubber systems would be needed. Thus, the costs of construction and operation and the areas required for Algal Turf Scrubber systems render them impractical for use in reducing the levels of dissolved nutrients in smaller bodies of water. In addition, Algal Turf Scrubber systems do not attempt to directly lower the levels of *E. coli* bacteria and pathogens such as *Salmonella*, Streptococci, *Cryptosporidium*, *Giardia*, and Enterovirus.

There is, therefore, a need in the industry for an apparatus and method for reducing the levels of dissolved nutrients, reducing the levels of *E. coli* bacteria and pathogens, improving water quality, and producing potable water from freshwater creeks, streams, rivers and lakes using little land or sea area, and that resolves the difficulties, shortcomings, and problems associated with using Algal Turf Scrubber systems or other technologies with smaller bodies of water.

SUMMARY OF THE INVENTION

Broadly described, the present invention comprises an algal system, including apparatuses and methods, for improving water quality through the use of algae. In example embodiments, the algal system comprises a water treatment device or cartridge including algae enclosed therein and capable of reducing at least the levels of nitrates and phosphates from contaminated water directed therethrough. In other example embodiments, the algal system comprises a water treatment device or cartridge including algae selected and enclosed therein that is capable of killing or reducing the levels of *E. coli* bacteria, other bacteria, viruses, parasites, fungi, and pathogens in contaminated water flowing therethrough, in addition to reducing the levels of nitrates and phosphates in the contaminated water. The algae is selected based on the particular chemical compounds, bacteria, viruses, parasites, fungi, pathogens, or other contaminants in the contaminated water, the amounts or levels of which are to be reduced by the algal system. And, the use of some algae may achieve better results in certain contamination situations and locations than in others. Hence, the algal system may be configured with and utilize different types of algae, and may be configured with and utilize different types of algae in different contamination situations and areas of the world. In still other example embodiments, the algal system comprises a water treatment device or cartridge that includes algae and other biological organisms selected and enclosed therein based on the type of contaminants to be reduced in contaminated water.

In accordance with a first example embodiment described herein and not for limitation, the algal system includes an elongate water treatment device defining a tubular chamber configured with a filamentous green algae therein. The elongate water treatment device includes a substantially hemispherical, or half dome, shaped filter therein on which the filamentous green algae grows and forms an algal turf, and through which water is directed. The algal system further comprises a pump configured to draw contaminated water at an appropriate volumetric flow rate from a body of water for treatment and to deliver the contaminated water to the elongate water treatment device. Preferably, the pump is powered with electrical energy provided by a solar photovoltaic panel or other similar device. The elongate water treatment device and substantially hemispherical shaped filter are sized and the volumetric flow rate of water is selected to cooperatively provide sufficient residence time for the contaminated water to be exposed to and come into contact with the algae, thereby enabling the algae to reduce the amounts or levels of dissolved nitrates and phosphates from the contaminated water.

According to a second example embodiment described herein and not for limitation, the algal system includes an elongate water treatment device defining a tubular chamber therein and an elongate cartridge defining a tubular chamber therein. The elongate water treatment device and elongate cartridge are configured for releasable connection therebetween such that the tubular chamber of the elongate cartridge is replaceable and configurable in fluid communication with the tubular chamber of the elongate water treatment device to enable contaminated water to flow through both tubular chambers. The elongate cartridge includes algae and, possibly, other biological organisms and even certain invertebrates therein. By pre-configuring the elongate cartridges with one or more particular types of algae and other chemicals, biological organisms, and/or other contents, elongate cartridges may be customized for subsequent delivery and use in any area of the world depending on the type and nature of contaminants, pH levels, characteristics, and/or properties in/of the contaminated water to be treated through use of the algal system. For example, cartridges may be pre-configured to reduce nitrates and phosphates from contaminated water, while also killing or reducing the level of *E. coli* bacteria, other bacteria, viruses, parasites, and fungi.

The elongate cartridge also includes a substantially hemispherical, or half dome, shaped filter therein on which algae grows and forms an algal turf, and through which contaminated water is directed after connection of the elongate cartridge to the elongate device. Similar to the algal system of the first example embodiment, the algal system of the second example embodiment additionally includes a pump configured to draw contaminated water at an appropriate volumetric flow rate from a contaminated body of water for treatment and to deliver the contaminated water to the coupled elongate device and elongate cartridge. Also similar to the algal system of the first example embodiment, the components of the algal system of the second example embodiment are sized and the volumetric flow rate of contaminated water is selected to cooperatively provide sufficient residence time for the contaminated water to be exposed to and come into contact with the algae and other contents of the cartridge, thereby enabling treatment of the contaminated water.

Advantageously, the algal system improves the water quality of smaller contaminated bodies of water than those typically treated by Algal Turf Scrubber systems and does so in a cost effective, economical manner. The algal system is easy to set up and operate, making the algal system usable by non-scientifically trained persons. Additionally, the algal system may be used in urbanized areas or in remote areas where electricity may or may not be available. In addition, after using the algal system for a period of time, the algal turf may be removed and sent off for conversion into biofuel such as, but not limited to, biodiesel, gasohol, methane, and butanol.

Other uses and benefits of the present invention may become apparent upon reading and understanding the present specification when taken in conjunction with the appended drawings.

BRIEF DESCRIPTION OF THE DRAWING

FIG. 4 displays a side, perspective view of a cartridge of an algal system for improving water quality in accordance with a second example embodiment of the present invention.

FIG. 5 displays an exploded view of the cartridge of FIG. 4.

DETAILED DESCRIPTION OF THE DRAWINGS

Figure 1:
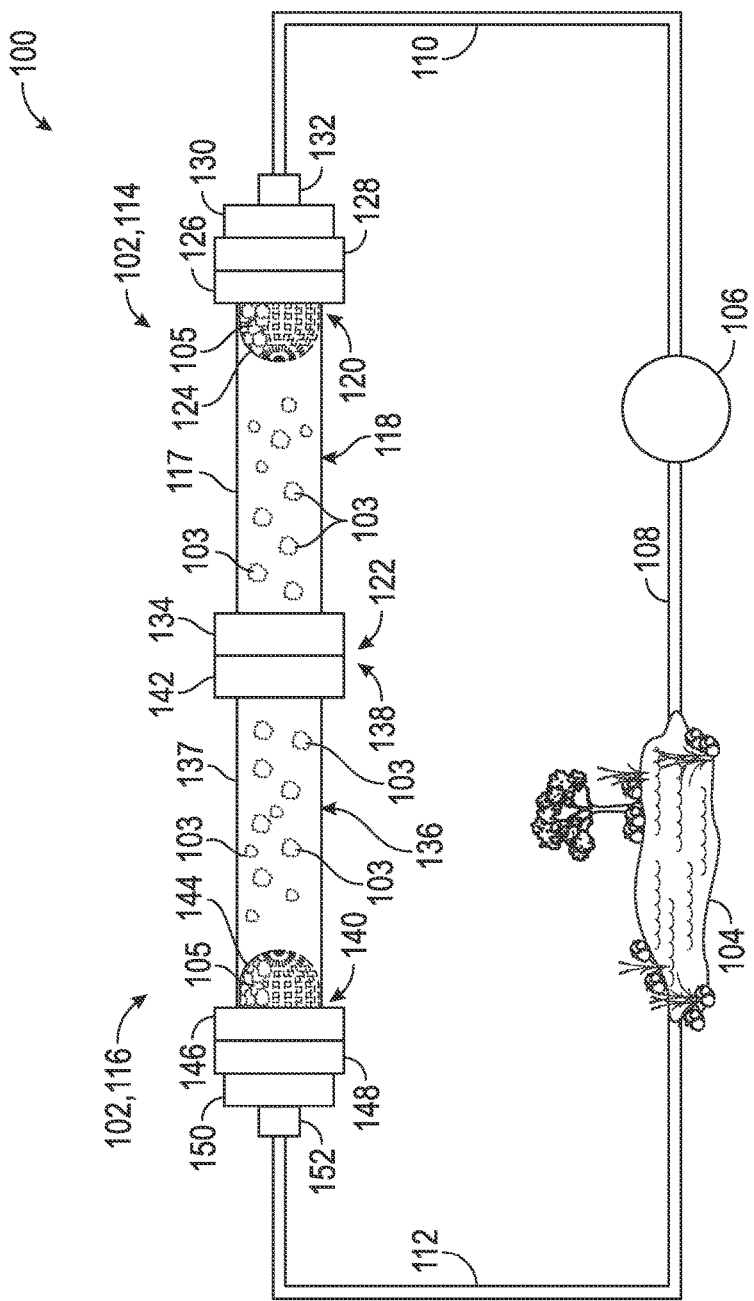
FIG. 1 displays a schematic view of an algal system for improving water quality and environment therefor in accordance with a first example embodiment of the present invention.

Referring now to the drawings in which like numerals represent like elements, FIG. 1 displays a schematic view of an algal system for improving water quality 100 and environment therefor in accordance with a first example embodiment of the present invention. The algal system for improving water quality 100 (also sometimes referred to herein as the "system for improving water quality 100" or "system 100") substantially reduces nitrate and phosphate levels, reduces bacteria (including, without limitation, *Escherichia coli*), virus, parasite, and fungi levels, increases dissolved oxygen levels, and maintains pH levels found in the contaminated water of bodies of water 104. Generally, as used herein, the terms "body of water" or "bodies of water" includes, but is not limited to, freshwater creeks, streams, ponds, and lakes.

The system 100, as illustrated in FIG. 1, comprises a water treatment device 102 configured with algae 103 therein to improve the water quality of contaminated water present in a body of water 104. Contaminants in the contaminated water may include, but not be limited to, (i) nitrogen, nitrates, and various nitrogen compounds, (ii) phosphorous, phosphates, and various phosphorous compounds, (iii) bacteria (including, without limitation, *Escherichia coli*), (iv) viruses, (v) parasites, and (vi) fungi. The system 100 also comprises a pump 106 and a suction hose 108 extending between the body of water 104 and pump 106 such that the body of water 104 and pump 106 are in fluid communication. Additionally, the system 100 comprises an intake hose 110 extending between the pump 106 and water treatment device 102 and placing the pump 106 and water treatment device 102 in fluid communication. In addition, the system 100 comprises a discharge hose 112 extending between the water treatment device 102 and the body of water 104 so that the water treatment device 102 and body of water 104 are in fluid communication.

The algae 103 comprises one or more type(s) of algae 103 selected based at least in part on the type of contaminants present in the contaminated water to be treated by the algal system 100. According to the first example embodiment and to remove nitrates and phosphates dissolved in the contaminated water as contaminants, the algae 103 includes filamentous green algae. One form of filamentous green algae, *Spirogyra grevilleana* (*S. grevilleana*) algae, has been found to be particularly successful in significantly decreasing levels of dissolved nutrients, including nitrates and phosphates dissolved in contaminated water. *Spirogyra* algae are a genus of the order Chlorophyta (green filamentous algae). *Spirogyra* algae grow in long many-celled, hair-like strands and are commonly found in freshwater areas with relatively clean eutrophic water. In addition to efficiently and quickly absorbing nutrients, *Spirogyra* spp. secrete unique and powerful excrements known as secondary metabolites. The secondary metabolites have various antibiotic effects ranging from antibacterial (gram positive and gram negative) to antiviral to antifungal. *Spirogyra* spp. reduce bacterial levels of *E. coli* and other aquatic bacteria (such as *Giardia* spp.), not only by reducing nutrient levels needed to sustain bacterial populations, but also by secreting their antibacterial compounds into the water. It should be appreciated and understood, however, that other types or forms of algae 103 having similar properties and characteristics may be acceptable in other embodiments, and that other types or forms of algae 103 may perform better in different areas of the world.

Figure 2:
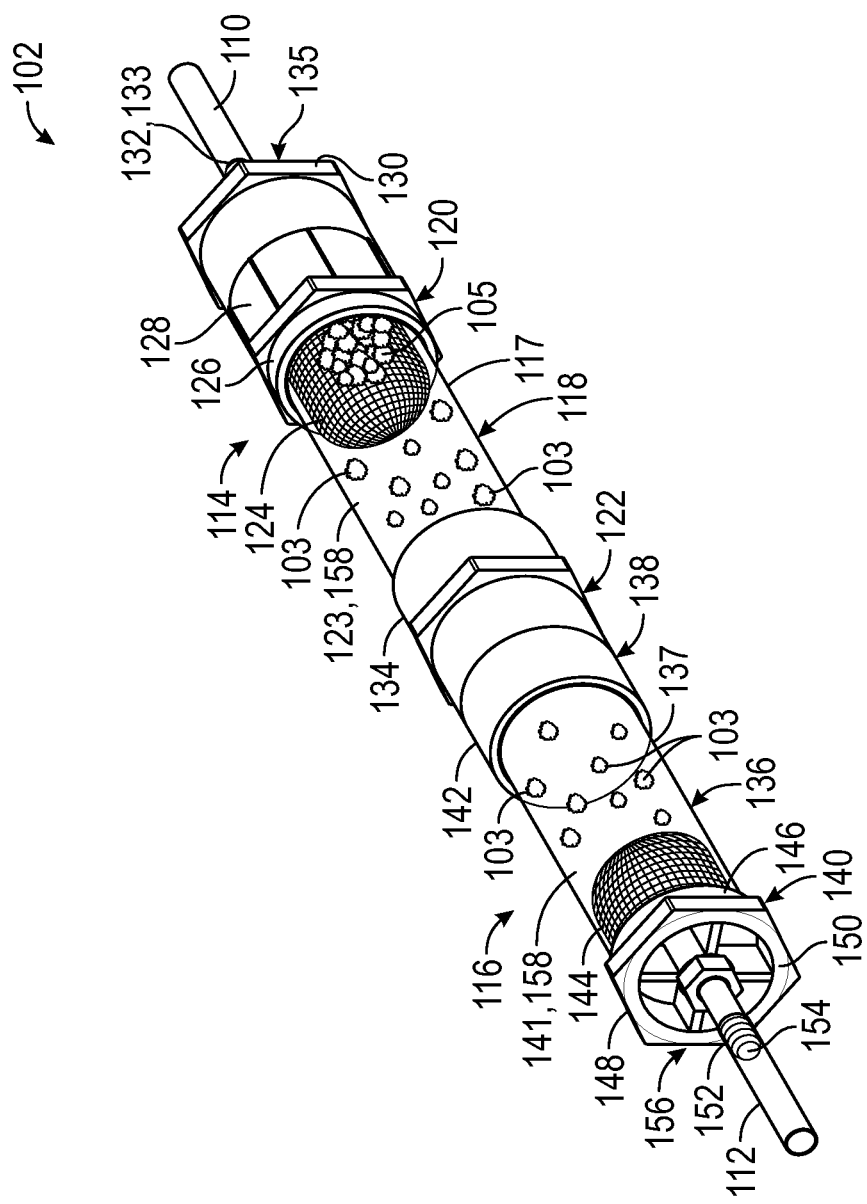
FIG. 2 displays a side, perspective view of a water treatment device of the algal system of FIG. 1 in accordance with the first example embodiment of the present invention.
Figure 3:
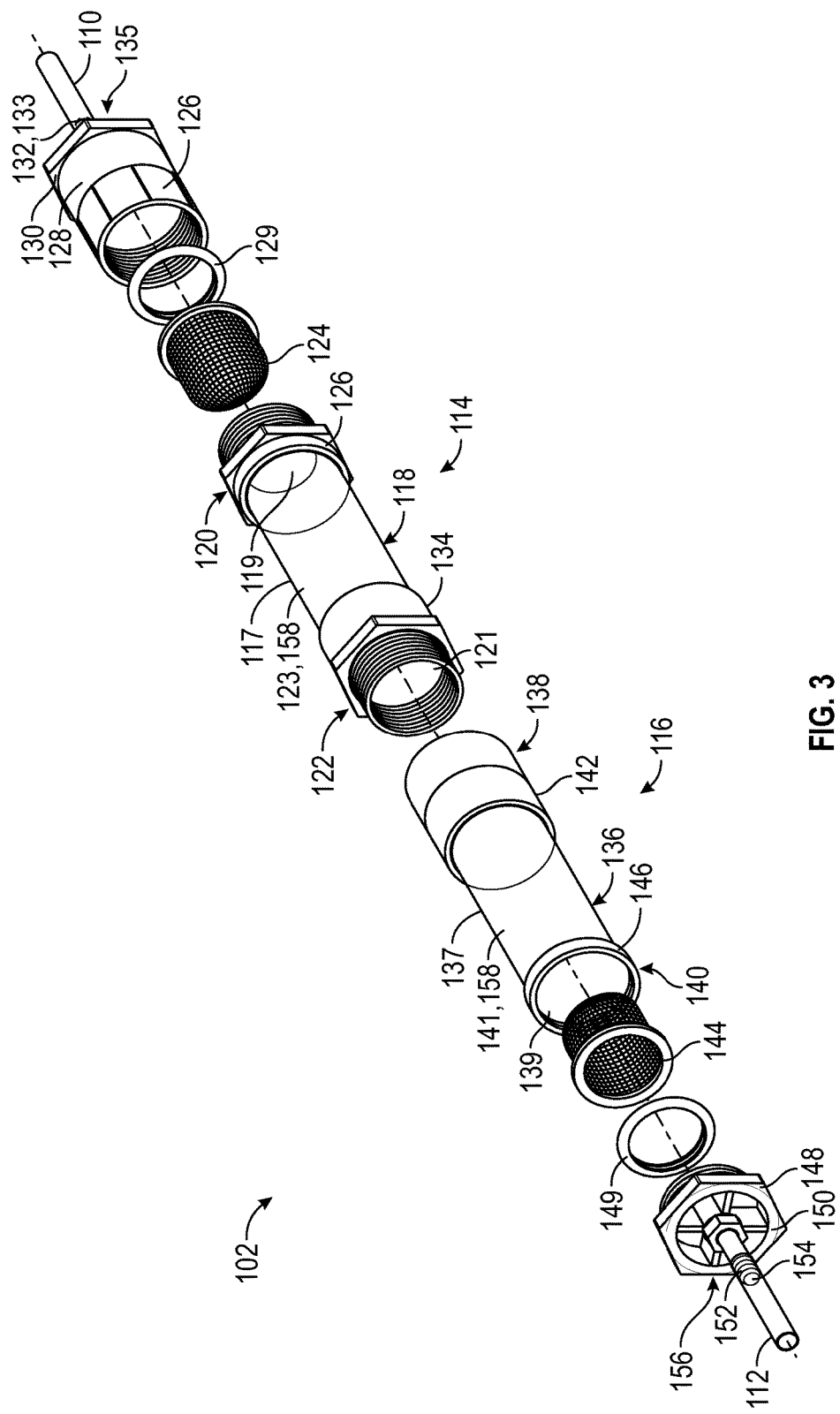
FIG. 3 displays an exploded view of the water treatment device of the algal system of FIG. 1 in accordance with the first example embodiment of the present invention.

As illustrated in FIGS. 1-3, the water treatment device 102 (also sometimes referred to herein as the "device 102") of the first example embodiment comprises a modular structure designed for ease of transportation, setup, use and maintenance. The device's structure includes a first segment 114 and a second segment 116 that are coupled together during setup and use, and that are separated from one another for transportation of the device 102 between locations. The second segment 116 is substantially a mirror image of the first segment 114 with the exception that the first segment 114 includes a threaded male coupling 134 and the second segment 116 includes a threaded female coupling 142 for releasably joining the first and second segments 114, 116 together. When connected together, the first and second segments 114, 116 are in fluid communication, permitting contaminated water being treated to flow from the first segment 114 into the second segment 116 through couplings 134, 142.

The device's first segment 114 comprises a tubular elongate member 118 having a generally cylindrically-shaped wall 117 extending between a first end 120 and a distant second end 122. The elongate member 118 defines a first opening 119 at the first end 120, a second opening 121 at the second end 122, and an elongate chamber 123 extending between the first and second ends 120, 122 and between the first and second openings 119, 121. The first and second ends 120, 122, first and second openings 119, 121, and elongate chamber 123 are in fluid communication such that when contaminated water is being treated by the device 102, the contaminated water flows within the elongate chamber 123 from the first end 120 toward the second end 122. The elongate member 118 is manufactured from a durable, relatively shock resistant material capable of transmitting therethrough all, or substantially all, of the wavelengths of light incident upon the water treatment device 102 during use of the system 100 that are suitable for photosynthesis and growing of the algae 103. A material, acceptable in accordance with the first example embodiment, includes clear polyvinyl chloride (PVC), but other materials having a high light transmissivity may alternatively be used.

Also, the device's first segment 114 includes an algae filter 124 positioned within the segment's elongate chamber 123 near the segment's first end 120. The algae filter 124 is removably secured in position by a fitting 126 attached to the elongate member 118 proximate the segment's first end 120. The algae filter 124 is removably secured by fitting 126 to enable removal of the algae filter 124 for cleaning and maintenance. According to the first example embodiment, the algae filter 124 has a generally hemispherical, or dome, shape (similar to that of a tea filter of a tea pot) and formed from a wire mesh or plastic mesh that are both cooperatively selected and sized to cause the appropriate buildup thereon of an algal cake 105 (or algal turf 105) during operation of the system 100. The hemispherical shape of the algae filter 124 was selected because such a hemispherical shape causes the algae filter 124 to provide substantial surface area for the buildup of an algal turf 105 thereon relative to the overall size of the algae filter 124. It should be appreciated and understood that, in other embodiments, the algae filter 124 may have the same shape or a different shape that provides substantial surface area for the buildup of an algal turf 105 thereon.

Another fitting 128 of the first segment 114 is releasably secured to fitting 126 and receives a rubber washer 129 (to aid in preventing water leakage from the device 102) and a plug 130 therein. An appropriately-sized barbed adapter 132 is mounted to and extends from the plug 130 for connection to the system's intake hose 110 during setup and operation of the system 100. The barbed adapter 132 and a hole 133 in the outboard end of the barbed adapter 132 form an intake port 135 of the water treatment device 102. The algae filter 124, fittings 126, 128, plug 130, and barbed adapter 132 are in fluid communication such that during the system's operation, contaminated water being treated flows from the intake hose 110 and through the hole 133 in the barbed adapter 132, the barbed adapter 132, plug 130, fittings 126, 128, and algae filter 124 into the segment's elongate chamber 123. A threaded male coupling 134 is secured to elongate member 118 at the segment's second end 122 to enable the water treatment device's first segment 114 to be releasably connected to the device's second segment 116.

In substantially a mirror image to the first segment 114, the device's second segment 116 comprises a tubular elongate member 136 having a generally cylindrically-shaped wall 137 extending between a first end 138 and a distant second end 140. The elongate member 136 defines a first opening (not visible) at the first end 138, a second opening 139 at the second end 140, and an elongate chamber 141 extending between the first and second ends 138, 140 and between the first opening and second opening 139. The first and second ends 138, 140, first opening, second opening 139, and elongate chamber 141 are in fluid communication such that when contaminated water is being treated by the device 102, the contaminated water flows within the elongate chamber 141 from the first end 138 toward the second end 140. The elongate member 136 is manufactured from a durable, relatively shock resistant material capable of transmitting therethrough all, or substantially all, of the wavelengths of light incident upon the water treatment device 102 during use of the system 100 that are suitable for or contributed to photosynthesis and growth of the algae 103. A material, acceptable in accordance with the example embodiment, includes clear polyvinyl chloride (PVC), but other materials having a high light transmissivity may alternatively be used.

The second segment 116 includes a threaded female coupling 142 secured to elongate member 136 at the segment's first end 138 to enable the water treatment device's second segment 116 to be releasably connected to the device's first segment 114. When so connected, the first segment's elongate chamber 123 and the second segment's elongate chamber 141 are in fluid communication and define a water treatment chamber 158 where contaminated water being treated is exposed to algae 103. The second segment 116 also includes an algae filter 144 positioned within the segment's elongate chamber 141 near the segment's second end 140. The algae filter 144 is removably secured in position by a fitting 146 attached to the elongate member 136 proximate the segment's second end 140. The algae filter 144 is removably secured by fitting 146 to enable removal of the algae filter 144 for cleaning and maintenance. According to the first example embodiment, the algae filter 144 has a generally hemispherical, or dome, shape (similar to that of algae filter 124) and formed from a wire mesh (or plastic mesh) that are both cooperatively selected and sized to cause the appropriate buildup thereon of an algal cake 105 (or algal turf 105) during operation of the system 100. The hemispherical shape of the algae filter 144 was selected because a hemispherical shape causes the algae filter 144 to provide substantial surface area for the buildup of an algal turf 105 thereon relative to the overall size of the algae filter 144. It should be appreciated and understood that, in other embodiments, the algae filter 144 may have the same shape or a different shape that provides substantial surface area for the buildup of an algal turf 105 thereon.

Another fitting 148 of the second segment 116 is releasably secured to fitting 146 and receives a rubber washer 149 (to aid in preventing water leakage from the device 102) and a plug 150 therein. An appropriately-sized barbed adapter 152 is mounted to the plug 150 for connection to the system's discharge hose 112 during setup and operation of the system 100. The barbed adapter 152 and a hole 154 in the outboard end of the barbed adapter 152 form a discharge port 156 of the water treatment device 102. The algae filter 144, fittings 146, 148, plug 150, barbed adapter 152, and hole 154 of the barbed adapter 152 are in fluid communication such that during the system's operation, contaminated water being treated flows from the segment's elongate chamber 141 and through the algae filter 144. After flowing through fittings 146, 148, plug 150, and adapter 152, the now treated and less contaminated water flows into the discharge hose 112 and back into the body of water 104.

It should be appreciated and understood that couplings 134, 142, fittings 126, 128, 146, 148 and plugs 130, 150 are also generally manufactured from a durable, relatively shock resistant material. If possible, such components should be manufactured from a material that permits transmission therethrough of all, or substantially all, of the light incident upon the water treatment device 102 during use, and especially those wavelengths of light that contribute to photosynthesis and growth of algae 103. A material for such components, acceptable according the example embodiment, includes clear polyvinyl chloride (PVC). Other clear plastic or acrylic materials may also be used. However, in alternate embodiments, such components may be manufactured from an opaque material such as opaque polyvinyl chloride (PVC) or other opaque plastic or acrylic materials, and without substantial degradation in the performance of the system 100 in treating contaminated water.

It also should be appreciated and understood that the pump 106, suction hose 108, intake hose 110, and discharge hose 112 are generally sized relative to the water treatment device 102 to permit a desired flow rate of contaminated water from the body of water 104 to be treated by the system 100 in a particular implementation. Thus, for example, in systems 100 capable of treating small flow rates of contaminated water from the body of water 104, the pump 106 may have a small impeller driven by a fractional horsepower electric motor at a relatively low rotational speed and the suction hose 108, intake hose 110 and discharge hose 112 may comprise rubber tubing. Alternatively, for example, in systems 100 capable of treating larger flow rates of contaminated water from the body of water 104, the pump 106 may have a larger impeller driven at a faster rotational speed by a multi-horsepower electric motor and the suction hose 108, intake hose 110 and discharge hose 112 may comprise rubber hoses or plastic (or metal) pipes having diameters of multiple inches. It should also be appreciated and understood that electrical power for operating the pump 106 may be supplied by electrical connection of the pump's motor to a utility electrical power grid or to an appropriately sized and configured photovoltaic solar power system that may include batteries to store and supply electrical power to the pump's motor at night or at other times when sufficient sunlight is unavailable.

The system 100 is configured for operation by inserting algae 103 into one of the elongate members 118, 136, placing pipe sealing tape around the threads of coupling 134, and threadably engaging couplings 134, 142 until the couplings 134, 142 are fully tightened together. When so configured, the algae 103 and contaminated water being treated may spread and/or flow throughout the elongate water treatment chamber 158 formed by the elongate chambers 123, 141 of the elongate members 118, 136. However, the algae 103 cannot pass through algae filters 124, 144 and is, hence, trapped within the elongate water treatment chamber 158.

After insertion of the algae 103, one end of the suction hose 108 is placed into the body of water 104 from which contaminated water is to be drawn for treatment. The other end of the suction hose 108 is connected to the intake port of the pump 106. Then, one end of the intake hose 110 is connected to the discharge port of the pump 106. The other end of the intake hose 110 is connected to barbed adapter 132 and the device's intake port 135. Next, one end of the discharge hose 112 is connected to barbed adapter 152 and the device's discharge port 156. The other end of the discharge hose 112 is placed into the body of water 104 so that treated water is returned to the body of water 104.

Once the hoses are connected, electrical power is supplied to the pump 106, causing the pump 106 to pull contaminated water in from the body of water 104 and direct such contaminated water to the water treatment device 102. As the contaminated water flows into and through the device's water treatment chamber 158 and algae filters 124, 144, the contaminated water passes through algae filter 124 coming into contact with algae 103 and an algal turf 105 of algae 103 that builds up on the algae filter 124. The algae 103 reduces the levels of nutrients in the forms of nitrogen and phosphorous from the contaminated water as "food" and, hence, reduces the levels of such nutrients in the contaminated body of water 104, causing algae 103 in the body of water 104 to starve and die off. Additionally, by virtue of the walls of the elongate members 118, 136 allowing light having wavelengths suitable for photosynthesis to pass therethrough, the algae performs photosynthesis and grows within the water treatment chamber 158 and on the algae filters 124, 144 to form an algal turf 105 thereon. Because the contaminated water must pass through the algae filters 124, 144 and algal turfs 105 thereof, the time duration and level of exposure of the contaminated water to the algae 103 is enhanced, thereby improving the amount of contaminants that are removed from the contaminated water.

The system 100 may remain in place at a particular contaminated body of water 104 to continually provide treatment thereof. From time-to-time, it may be desirable to clean the water treatment device 102 and the algae filters 124, 144 thereof to lessen the thickness of the algal turfs 105 built up thereon. The removed algae 103 may be sent to a processing facility and converted into a biofuel such as biodiesel, gasohol, methane, and butanol. After cleaning is complete, new algae 103 is inserted into the water treatment device 102 as described above and the device 102 is reassembled to again operate to treat contaminated water of the body of water 104.

According to a second example embodiment, the algal system 100' is substantially similar to the algal system 100 of the first example embodiment and includes the components thereof with the exception that the algal system 100' further comprises one or more cartridges 180' and a water treatment device 102' differently configured to replaceably receive a cartridge 180' therein. Each cartridge 180' is independently configured and customizable with algae 103' of one or more particular types and, possibly, with other biological organisms that are selected and enclosed therein based at least in part on the types of contaminants to be reduced in contaminated water at a particular location. Cartridges 180' may be configured and delivered to the site of a contaminated body of water for insertion into a water treatment device 102' already present at the site. Once delivered, an existing no longer useable cartridge 180' is removed from the water treatment device 102' and replaced with the newly delivered cartridge 180'. When connected together, the cartridge 180' and water treatment device 102' are in fluid communication, permitting contaminated water being treated to flow through the cartridge 180' and water treatment device 102'.

Similar to the first example embodiment and if the contaminants in the contaminated water include dissolved nitrogen and phosphorous, the algae 103' includes a form of filamentous green algae such as, but not limited to, *Spirogyra grevilleana* (*S. grevilleana*) algae. As described above, in addition to efficiently and quickly absorbing nutrients such as nitrates and phosphates, *Spirogyra* spp. secrete unique and powerful excrements known as secondary metabolites. The secondary metabolites have various anti-pathogenic effects ranging from antibacterial (gram positive and gram negative) to antiviral to antifungal. *Spirogyra* spp. reduce bacterial levels of *E. coli* and other aquatic bacteria (such as *Giardia* spp.), not only by reducing nutrient levels needed to sustain bacterial populations, but also by secreting their antibacterial compounds into the water. *Spirogyra* spp. may also reduce levels of viruses, parasites and fungi present in contaminated water.

FIGS. 4 and 5 respectively display side, perspective and exploded views of a cartridge 180' of the algal system 100' of the second example embodiment. The cartridge 180' comprises a tubular elongate member 182' having a first end 184' and a distant second end 186'. The elongate member 182' has a generally cylindrically-shaped wall 188' that defines a first opening 190' at the first end 184', a second opening 192' at the second end 186', and an elongate chamber 194' extending between the first and second ends 184', 186' and between the first and second openings 190', 192'. One or more types of algae 103' and, possibly, other biological organisms reside within the elongate chamber 194'. The algae 103' and biological organisms are selected and included within the elongate chamber 194' based at least in part on the particular contaminants present in the contaminated water to be treated by the algal system 100' and, possibly, on the location of the site at which the algal system 100' will be used. The first and second ends 184', 186', first and second openings 190', 192', and elongate chamber 194' are in fluid communication such that when contaminated water is being treated by the system 100', the contaminated water flows within the elongate chamber 194' from the first end 184' toward the second end 186'. The elongate member 182' and wall 188' thereof is manufactured from a durable, relatively shock resistant material capable of transmitting therethrough all, or substantially all, of the wavelengths of light incident upon the water treatment device 102' during use of the system 100' that are suitable for photosynthesis and growing of algae 103'. A material, acceptable in accordance with the second example embodiment, includes clear polyvinyl chloride (PVC), but other materials having a high light transmissivity may alternatively be used.

The cartridge 180' includes first and second male threaded couplings 196', 198' secured to the elongate member 182', respectively, at the elongate member's first and second ends 184', 186'. The cartridge 180' also includes first and second algae filters 200', 202' having rims 205', 207' that abut, respectively, against the first and second male threaded couplings 196', 198' near the elongate member's first and second ends 184', 186'. The algae filters 200', 202' respectively protrude into the elongate chamber 194' from the elongate member's first and second ends 184', 186' and receive light passing through the cartridge's wall 188'. According to the second example embodiment, the algae filters 200', 202' have a generally hemispherical, or dome, shape (similar to that of a tea filter of a tea pot) and are formed from a wire mesh (or plastic mesh) that are both cooperatively selected and sized to cause the appropriate buildup thereon of an algal cake 105' (or algal turf 105') during operation of the algal system 100'. The hemispherical shape of the algae filters 200', 202' was selected because such a hemispherical shape causes the algae filters 200', 202' to provide substantial surface area for the buildup of an algal turf 105' thereon relative to the overall size of the algae filters 200', 202'. It should be appreciated and understood that, in other embodiments, one or both of the algae filters 200', 202' may have a different shape that provides substantial surface area for the buildup of an algal turf 105' thereon.

The cartridge 180' also includes rubber washers 204', 206' that abut respective rims 205', 207' of the algae filters 200', 202'. The rubber washers 204', 206' and algae filters 200', 202' are releasably held in position by respective end caps 208', 210'. The end caps 208', 210' have internal female threads that are operative to receive the male threads of the first and second male threaded couplings 196', 198'. Together, the rims 205', 207', rubber washers 204', 206', and end caps 208', 210' aid in preventing water and/or algae 103' leakage from the cartridge 180' during delivery or storage of the cartridge 180'.

Figure 6:
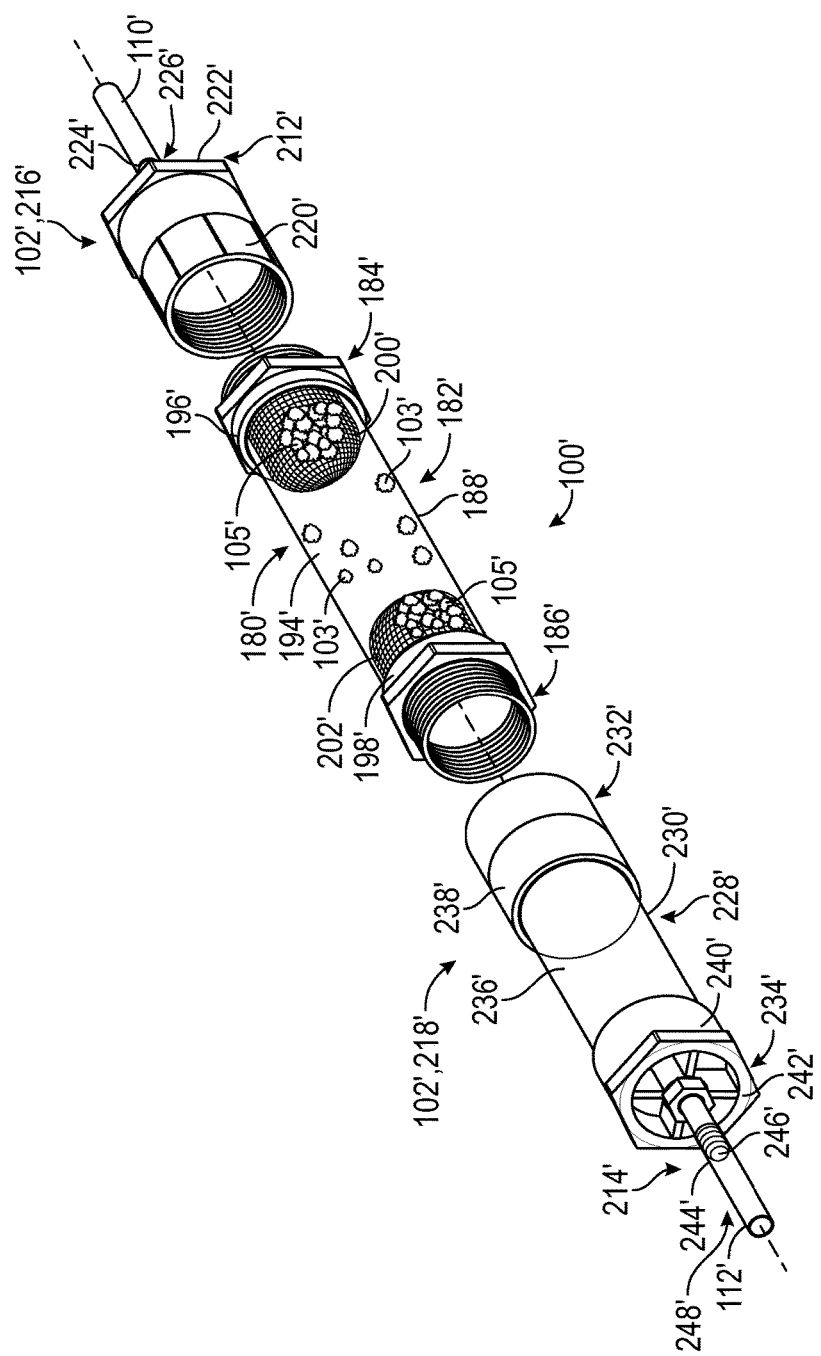
FIG. 6 displays an exploded view of the cartridge of FIG. 4 illustrating the position of the cartridge after insertion into a water treatment device of the algal system for improving water quality in accordance with the second example embodiment of the present invention.

FIG. 6 displays an exploded view of the cartridge 180' after insertion into a water treatment device 102' of the algal system 100' in accordance with the second example embodiment. The water treatment device 102' (also sometimes referred to herein as "device 102'") comprises a generally elongate modular structure operable with a cartridge 180' and designed for ease of transportation, setup, use and maintenance. The water treatment device 102' has a first end 212' and distant second end 214', and includes a first portion 216' and a second portion 218' between which a cartridge 180' (absent end caps 208', 210') is inserted and coupled during use. When connected together, the first and second portions 216', 218' and cartridge 180' are in fluid communication, permitting contaminated water being treated to flow from the first portion 216', through the cartridge 180', and into the second portion 218' before being discharged from the water treatment device 102' as treated water.

The first portion 216' of the water treatment device 102' comprises a female coupling 220' having internal threads. The female coupling 220' receives a plug 222' having male threads therein at the first end 212' of the water treatment device 102'. An appropriately-sized barbed adapter 224' (partially visible) is mounted to and extends from the plug 222' for connection to the system's intake hose 110' during setup and operation of the system 100'. The barbed adapter 224' and a hole (not visible) in the outboard end of the barbed adapter 224' form an intake port 226' of the water treatment device 102'. The female coupling 220' also receives a portion of the cartridge's first male threaded coupling 196' therein such that the female coupling 220' and first male threaded coupling 196' are threadably engaged. When so engaged, rubber washer 204' and algae filter 200' are releasably held in position by cooperation between the female coupling 220' and the first male threaded coupling 196'.

The second portion 218' of the water treatment device 102' comprises a tubular elongate member 228' having a first end 230' and a distant second end 232'. The elongate member 228' has a generally cylindrically shaped wall 230' that defines a first opening (not visible) at the first end 232', a second opening (not visible) at the second end 234', and an elongate chamber 236' extending between the first and second ends 232', 234' and between the first opening and second opening. The first and second ends 232', 234', first and second openings, and elongate chamber 236' are in fluid communication such that when contaminated water is being treated by the system 100' and treated water is received from the cartridge 180', the treated water flows within the elongate chamber 236' from the first end 232' toward the second end 234'.

The second portion 218' also includes a first threaded female coupling 238' secured to elongate member 228' at the member's first end 232' to enable the water treatment device's second portion 218' to be releasably connected to the cartridge 180'. The first female coupling 238' receives a portion of the cartridge's second male threaded coupling 198' therein such that the first female coupling 238' and second male threaded coupling 198' are threadably engaged. When so engaged, rubber washer 206' and algae filter 202' are releasably held in position by cooperation between the first female coupling 238' and the second male threaded coupling 198'. Additionally, when so engaged, the cartridge's elongate chamber 194' and the second portion's elongate chamber 236' are in fluid communication.

Additionally, the second portion 218' of the water treatment device 102' includes a second threaded female coupling 240' secured to elongate member 228' at the member's second end 234'. The second threaded female coupling 240' receives a plug 242' having male threads therein at the second end 214' of the water treatment device 102'. An appropriately-sized barbed adapter 244' is mounted to and extends from the plug 242' for connection to the system's discharge hose 112' during setup and operation of the system 100'. The barbed adapter 244' and a hole 246' in the outboard end of the barbed adapter 244' form a discharge port 248' of the water treatment device 102'. The second threaded female coupling 240', plug 242', barbed adapter 244', and hole 246' of the barbed adapter 244' are in fluid communication such that during the system's operation, treated water flows from the second portion's elongate chamber 236' and through the second threaded female coupling 240', plug 242', barbed adapter 244', and hole 246', the now treated and less contaminated water flows into the discharge hose 112' and back into the body of water 104'.

It should be appreciated and understood that elongate member 228', couplings 220', 238', 240' and plugs 222', 242' are also generally manufactured from a durable, relatively shock resistant material. If possible, such components should be manufactured from a material that permits transmission therethrough of all, or substantially all, of the light incident upon the water treatment device 102' during use, and especially those wavelengths of light that contribute to photosynthesis and growth of algae 103'. A material for such components, acceptable according the example embodiment, includes clear polyvinyl chloride (PVC). Other clear plastic or acrylic materials may also be used. However, in alternate embodiments, such components may be manufactured from an opaque material such as opaque polyvinyl chloride (PVC) or other opaque plastic or acrylic materials, and without substantial degradation in the performance of the algal system 100' in treating contaminated water.

The algal system 100' of the second example embodiment is configured for operation by inserting a cartridge 180' pre-filled with algae 103' and, possibly, other biological organisms into the water treatment device 102'. To do so, the end caps 208', 210' are removed from the cartridge 180' and a portion of the cartridge's first male threaded coupling 196' is inserted into and threadably engaged with the female coupling 220' of the device's first portion 216'. The rubber washer 204' and algae filer 200' are held in position by the female coupling 220' and the cartridge's first male threaded coupling 196'. Then, a portion of the cartridge's second male threaded coupling 198' is inserted into and threadably engaged with the first female coupling 238' of the device's second portion 218'. Such engagement holds rubber washer 206' and algae filter 202' in position and results in the cartridge's elongate chamber 194' and the second portion's elongate chamber 236' being in fluid communication. However, even though the cartridge's elongate chamber 194' and the second portion's elongate chamber 236' are in fluid communication, the algae 103' remains trapped within the cartridge's elongate chamber 194' between algae filters 200', 202'.

After insertion of the cartridge 180', one end of the suction hose 108' is placed into the body of water 104' from which contaminated water is to be drawn for treatment. The other end of the suction hose 108' is connected to the intake port of the pump 106'. Then, one end of the intake hose 110' is connected to the discharge port of the pump 106'. The other end of the intake hose 110' is connected to barbed adapter 224' and the device's intake port 226'. Next, one end of the discharge hose 112' is connected to barbed adapter 244' and the device's discharge port 248'. The other end of the discharge hose 112' is placed into the body of water 104' so that treated water is returned to the body of water 104'.

Once the hoses 110', 112' are connected, electrical power is supplied to the pump 106', causing the pump 106' to pull contaminated water in from the body of water 104' and direct such contaminated water to the water treatment device 102'. As the contaminated water flows into and through the cartridge's elongate chamber 194' and algae filters 200', 202', the contaminated water comes into contact with algae 103' and algal turfs 105' of algae 103' that build up on the algae filters 200', 202'. The algae 103' reduces the levels of nutrients in the forms of nitrogen and phosphorous from the contaminated water as "food" and, hence, reduces the levels of such nutrients in the contaminated body of water 104', causing algae in the body of water 104' to starve and die off. Additionally, by virtue of the wall 188' of the cartridge's elongate member 180' allowing light having wavelengths suitable for photosynthesis to pass therethrough, the algae 103' performs photosynthesis and grows within the cartridge's elongate chamber 194' and on the algae filters 200', 202' to form algal turfs 105' thereon. Because the contaminated water must pass through the algae filters 200', 202' and algal turfs 105' thereof, the time duration and level of exposure of the contaminated water to the algae 103' is enhanced, thereby improving the amount of contaminants that are removed from the contaminated water.

The non-cartridge components of the algal system 100' of the second example embodiment generally remain at a site where contaminated water of a body of water 104' is being treated. However, after a period of operation, the cartridge 180' of the algal system 100' may require maintenance or be no longer providing desired water treatment performance. In either event, the cartridge 180' is removed from the water treatment device 102' by reversing the steps used to insert the cartridge 180' described above. A new cartridge 180' is then inserted into the water treatment device 102' and water treatment continued. The removed cartridge 180' is sent to a processing facility where the algae 103' and algal turfs 105' are removed and converted into a biofuel such as biodiesel, gasohol, methane, and butanol. Once the algae 103' and algal turfs 105' have been removed and converted, the removed cartridge 180' may be re-configured for subsequent use by loading the cartridge 180' with algae 103' and, possibly, other biological organisms appropriate for the body of water 104' with which the cartridge 180' will be used. Then, the re-configured cartridge 180' is delivered to the site of the body of water 104' to be treated and, ultimately, inserted into a water treatment device 102' at such site.

Further information pertaining to the algal system 100 and the operation thereof is included in the technical papers of Appendices A and B submitted with the application.

Whereas the present invention has been described in detail above with respect to example embodiments thereof, it should be appreciated that variations and modifications might be effected within the spirit and scope of the present invention.

What is claimed is:

1. An apparatus for improving water quality of a body of contaminated water, said apparatus comprising:
   a portable water treatment device movable from a first body of contaminated water to a second body of contaminated water and comprising a cylindrical wall formed from a material allowing the passage of light therethrough suitable for growing algae, said wall defining a substantially enclosed chamber therein for treating contaminated water received from a body of contaminated water to be treated, said portable water treatment device further comprising a water permeable structure protruding entirely within said chamber and having an algal turf growing thereon for requiring substantially all received contaminated water to pass through said water permeable structure and said algal turf;
   wherein said algal turf comprises algae adapted for removing nitrogen and phosphorous dissolved in water.

2. The apparatus of claim 1, wherein said water permeable structure protrudes into said chamber and has a permeable surface extending entirely within said chamber, and wherein the received contaminated water flows through said water permeable surface of said water permeable structure and said algal turf in a direction predominantly perpendicular to said water permeable surface at each opening where the received contaminated water flows therethrough.

3. The apparatus of claim 1, wherein said water permeable structure is manufactured from a wire mesh.

4. The apparatus of claim 1, wherein said water permeable structure is manufactured from a plastic mesh.

5. The apparatus of claim 1, wherein said water permeable structure has a substantially hemispherical shape.

6. The apparatus of claim 1, wherein said portable water treatment device has an intake port for receiving contaminated water from the body of contaminated water to be treated and for directing the received contaminated water to said water permeable structure and algal turf, and wherein said water permeable structure is configured and positioned relative to said intake port so as to require substantially all received contaminated water to pass through said structure and said algal turf.

7. The apparatus of claim 1, wherein said algae comprises a filamentous green algae.

8. The apparatus of claim 7, wherein said algae comprises *Spirogyra grevilleana* algae.

9. The apparatus of claim 1, wherein said cylindrical wall is formed from a clear polyvinyl chloride material.

10. The apparatus of claim 1, wherein said portable water treatment device has a discharge port for discharging treated water from said portable water treatment device, wherein said intake port, said discharge port, and said chamber are in fluid communication, and wherein said intake port and said discharge port are in fluid communication with the body of contaminated water being treated by said portable water treatment device.

11. The apparatus of claim 1, wherein said algae is further adapted to secrete secondary metabolites capable of killing bacteria.

12. The apparatus of claim 1, wherein said algae is further adapted to secrete secondary metabolites capable for killing viruses.

13. The apparatus of claim 1, wherein the apparatus further comprises a pump in fluid communication with said portable water treatment device for drawing water from the body of contaminated water to be treated and for directing the contaminated water to said portable water treatment device.

14. A portable system for improving water quality of a body of contaminated water, said portable system comprising:
  a portable water treatment device movable between bodies of contaminated water and including an intake port for receiving contaminated water from a source of contaminated water to be treated, wherein the received contaminated water has at least one contaminant therein, said portable water treatment device further including a discharge port for discharging treated water; and
  a removable, replaceable cartridge extending directly between said intake port of said water treatment device and said discharge port of said water treatment device with said intake port in fluid communication with said discharge port via said cartridge, said cartridge comprising a wall formed from a material allowing the passage of light therethrough suitable for growing algae, said wall defining a substantially enclosed chamber therein for receiving contaminated water directly from said intake port of said water treatment device and for directing treated water directly to said discharge port of said water treatment device after passage through said chamber, said cartridge further comprising a water permeable structure within said chamber having an algal turf growing thereon and configured within said chamber for requiring substantially all of the received contaminated water to pass therethrough, said algal turf comprising algae specifically selected and suitable for reducing the amount of the at least one contaminant in the received contaminated water;
  wherein said water permeable structure has a side extending entirely within said chamber, and wherein the received contaminated water flows through said side of said water permeable structure and said algal turf in a direction predominantly perpendicular to said side of said water permeable structure at each opening where the received contaminated water flows therethrough.

15. The system of claim 14, wherein the at least one contaminant comprises dissolved nitrogen.

16. The system of claim 14, wherein the at least one contaminant comprises dissolved phosphorous.

17. The system of claim 14, wherein the at least one contaminant comprises a bacterium.

18. The system of claim 17, wherein the algae is capable of producing secondary metabolites that cause a reduction in the amount of the at least one contaminant in the received contaminated water.

19. The system of claim 17, wherein the bacterium comprises *Escherichia coli*.

20. The system of claim 14, wherein the at least one contaminant comprises a virus.

21. The system of claim 20, wherein said algae is capable of producing secondary metabolites that cause a reduction in the amount of the at least one contaminant in the received contaminated water.

22. The system of claim 14, wherein said cartridge comprises a first removable, replaceable cartridge and is further configured for removal and replacement by a second removable, replaceable cartridge.

23. The system of claim 22, wherein said second cartridge is substantially similar to said first cartridge, and wherein said second cartridge comprises an algal turf within said chamber of said second cartridge including algae specifically selected and suitable for reducing the amount of the at least one contaminant in the received contaminated water.

24. The system of claim 22, wherein the at least one contaminant is a first contaminant and the received contaminated water has a second contaminant, wherein said second cartridge is substantially similar to said first cartridge, and wherein said second cartridge comprises an algal turf within said chamber of said second cartridge including algae specifically selected and suitable for reducing the amount of the second contaminant in the received contaminated water.

25. The system of claim 14, wherein said algae comprises a filamentous green algae.

26. The system of claim 25, wherein said algae comprises *Spirogyra grevilleana* algae.

27. The system of claim 14, wherein said water permeable structure protrudes into said chamber.

28. The system of claim 27, wherein said water permeable structure has a substantially hemispherical shape.

29. A method for improving water quality of a body of contaminated water, the method comprising the steps of:

directing contaminated water from a body of contaminated water into a substantially enclosed chamber of a device configured with an algal turf entirely in said chamber to remove a contaminant from the contaminated water;

causing substantially all of the contaminated water directed into the chamber to flow through the algal turf in a direction substantially perpendicular to a surface of the algal turf within said chamber; and returning the contaminated water after flowing through the algal turf and at least partial removal of the contaminant to the body of contaminated water.

30. The method of claim 29, wherein the algae comprises a filamentous green algae.

31. The method of claim 30, wherein the algae comprises *Spirogyra grevilleana* algae.

32. The method of claim 29, wherein the chamber comprises a bioreactor having a wall through which light having one or more wavelengths suitable for growth of the algal turf passes, wherein the wall at least partially defines a removeable, replaceable cartridge configured for removal and replacement of the algal turf.

33. The method of claim 29, wherein the contaminant comprises dissolved nitrogen.

34. The method of claim 29, wherein the contaminant comprises dissolved phosphorous.

35. The method of claim 29, wherein the contaminant comprises a bacterium.

36. The method of claim 35, wherein the bacterium comprises *Escherichia coli*.

37. The method of claim 29, wherein the contaminant comprises a virus.

* * * * *